US006908733B2

(12) United States Patent
Shah

(10) Patent No.: US 6,908,733 B2
(45) Date of Patent: Jun. 21, 2005

(54) DIAGNOSIS AND TREATMENT OF HUMAN KIDNEY DISEASES

(75) Inventor: Sudhir V. Shah, Little Rock, AR (US)

(73) Assignee: Shiva Biomedical, LLC, Paramus, NJ (US)

( * ) Notice: Subject to any disclaimer, the term of this patent is extended or adjusted under 35 U.S.C. 154(b) by 0 days.

(21) Appl. No.: 10/731,522

(22) Filed: Dec. 9, 2003

(65) Prior Publication Data

US 2004/0121422 A1 Jun. 24, 2004

Related U.S. Application Data

(62) Division of application No. 09/553,496, filed on Apr. 20, 2000.
(60) Provisional application No. 60/130,903, filed on Apr. 23, 1999, and provisional application No. 60/130,908, filed on Apr. 23, 1999.

(51) Int. Cl.[7] .............................. C12Q 1/00; C12Q 1/26
(52) U.S. Cl. ............................................. 435/4; 435/25
(58) Field of Search ........................................ 435/4, 25

(56) References Cited

U.S. PATENT DOCUMENTS

| 4,684,482 A | 8/1987 | Green |
| 5,047,329 A | * 9/1991 | Suzuki .................... 435/18 |
| 5,047,421 A | 9/1991 | Green |
| 5,091,180 A | 2/1992 | Walker et al. |
| 5,721,209 A | 2/1998 | Horwitz et al. |
| 5,811,127 A | 9/1998 | Milstein et al. |
| 6,206,849 B1 | 3/2001 | Martin et al. |
| 6,383,817 B2 | 5/2002 | Schwartz |
| 6,589,966 B1 | 7/2003 | Torti et al. |
| 6,706,287 B2 | 3/2004 | Ranganathan et al. |
| 2003/0064929 A1 | 4/2003 | Duranton et al. |

FOREIGN PATENT DOCUMENTS

| DE | 40 08 323 A | 9/1991 |
| JP | 05000949 A | 1/1993 |
| WO | WO 90/04584 | 5/1990 |
| WO | WO 91 07956 A | 6/1991 |
| WO | WO 94/01770 A | 1/1994 |
| WO | WO 00 13706 A | 3/2000 |
| WO | WO 00/54784 | 9/2000 |

OTHER PUBLICATIONS

Walker, P.D., et al., "Evidence Suggesting a Role for Hydroxyl Radical in Gentamicin–Induced Acute Renal Failure in Rats," *J Clin Invest* 81:334–341 (1988).
Shah, S.V., et al., "Evidence Suggesting a Role for Hydroxyl Radical in Glycerol–Induced Acute Renal Failure," *Am J Physiol* 255, (Renal Fluid Electrolyte Physiol. 24):F438–F443 (1988).
Baliga, R., et al., "Increase in Bleomycin–Detectable Iron in Ischaemia/Reperfusion Injury to Rat Kidneys," *Biochem J* 291 (3):901–905 (1993).
Kontoghiorghese, G.J., et al., "Studies of Aluminium Mobilization in Renal Dialysis Patients Using the Oral Chelator 1,2–Dimethyl–3–hydroxypyrid–4–one," *Arzneim–Forsh/Drug Res.* 44(1):522–526 (1994).
Baliga, R., et al., "Oxidant Mechanisms in Toxic Acute Renal Failure," *Drug Metabolism Reviews* 31(4):971–991 (1999).
Walker, P.D., et al., "Gentamicin Enhanced Production of Hydrogen Peroxide by Renal Cortical Mitochondria," *Am J Physiol* 253:C495–C499 (1987).
Walker, P.D., et al., "Hydrogen Peroxide Cytotoxicity in LLC–PK$_1$ Cells: A Role for Iron," *Kidney Int* 40:891–898 (1991).
Abul–Ezz, S.R., et al., "Role of Glutathione in an Animal Model of Myoglobinuric Acute Renal Failure," *Proc Natl Acad Sci* 88:9833–9837 (1991).
Ueda, N., et al., "Gentamicin–Induced Mobilization of Iron from Renal Cortical Mitochondria," *Am J Physiol* 265(3 Pt. 2):F435–F439 (1993).
Baliga, R., et al., "Evidence for Cytochrome P–450 as a Source of Catalytic Iron in Myoglobinuric Acute Renal Failure," *Kidney Int* 49:362–369 (1996).
Baliga, R., et al., "Role of Cytochrome P–450 as a Source of Catalytic Iron in Cisplatin–Induced Nephrotoxicity," *Kidney Int* 54:1562–1569 (1998).
Hanss, B.G., et al., "The Iron Chelator Deferoxamine Prevents Contrast Media Induced Acute Renal Failure in the Rabbit." Presented at the American Society of Nephrology, 23rd Annual Meeting, *JASN* 1(4):612 (1990) (abstract).
Baliga, R., et al., "Role of Iron in Cisplatin–Induced Acute Renal Failure in Rats," *J Am Soc Nephrol* 7(9):1822 (1996) (abstract).
Fernández–Real, J.M., et al., "Cross–Talk Between Iron Metabolism and Diabetes," *Diabetes*, 51:2348–2354, 2002.
Nitenberg, A., et al., "Coronary Microvascular Adaptation to Myocardial Metabolic Demand Can Be Restored by Inhibition of Iron–Catalyzed Formation of Oxygen Free Radicals in Type 2 Diabetic Patients," *Diabetes*, 51:813–818, 2002.

(Continued)

Primary Examiner—Susan Coe
Assistant Examiner—Randall Winston
(74) Attorney, Agent, or Firm—Hamilton, Brook, Smith & Reynolds, P.C.

(57) ABSTRACT

Kidney disease is diagnosed by measuring urinary catalytic iron in humans. Progressive kidney disease is treated by administering an iron chelator to humans. In particular, the progression of kidney disease essentially can be halted and the severity of kidney disease can be reduced by the administration of iron chelators to humans afflicted with a progressive kidney disease. The methods include measuring catalytic iron content in urine in a human afflicted with a progressive kidney disease and administering an iron chelator to the human. The method can include measuring total urinary protein content, blood urea nitrogen or creatinine in a blood sample before, during or after the administration of an iron chelator.

16 Claims, 1 Drawing Sheet

OTHER PUBLICATIONS

Sumboonnanonda, A., et al., "Renal tubular function in β–thalassemia", *Pediatr Nephrol*, 12:280–283.

Ong–ajyooth, L., et al., "Renal Function in Adult Beta–Thalassemia/Hb E Disease", *Nephron*, 78:156–161 (1998).

Guasch, A., et al., "Evidence that Microdeletions in the α Globin Gene Protect Against the Development of Sickle Cell Glomerulopathy in Humans", *J Am Soc Nephrol*, 10:1014–1019 (1999).

Loebstein, R., et al., "Diabetic Nephropathy in Hypertransfused Patients with β–Thalassemia", *Diabetes Care*, 21(8):1306–1309 (1998).

Ongajyooth, L., et al., "Glomerulonephritis in β–thalassemia Hb–E Disease: Clinical Manifestations, Histopathologic Studies and Outcome", *J Med Assoc Thai*, 78(3):119–126 (1995).

Aoki, R.Y., et al., "Microalbuminuria in Sickle Cell Disease", *Brazilian J Med Biol Res*, 23:1103–1106 (1990).

Katopodis, K.P., et al., "Renal Abnormalities in Patients with Sickle Cell–Beta Thalassemia", *Journal of Nephrology*, 10(3):163–167 (1997).

Pham, P.–T.T., et al., "Renal abnormalities in sickle cell disease", *Kidney International*, 57:1–8 (2000).

Kontoghiorghes, G.J., et al., "Simple Synthesis of the Potent Iron Clelators 1–Alkyl–3–hydroxy–2–methylpyrid–4–ones", *Inorganica Chimica Acta.*, 136:L11–L12 (1987).

Falk, R.J., et al., "Prevalence and Pathologic Features of Sickle Cell Nephropathy and Response to Inhibition of Angiotensin–Convertng Enzyme", *The New England Journal of Medicine*, 326(14):910–915 (1992).

Guasch, A., et al., "Sickle cell anemia causes a distinct pattern of glomerular dysfunction", *Kidney International*, 51:826–833 (1997).

Cianciulli, P., et al., "Early detection of nephrotoxic effets in thalassemic patients receiving desferrioxamine therapy", *Kidney International*, 46:467–470 (1994).

Ueda, N., et al., "Role of 'catalytic' iron in an animal model of minimal change nephrotic syndrome", *Kidney International*, 49:370–373 (1996).

Savill, J., et al., "Mechanisms of glomerular injury". In "Oxford Textbook of Clinical Nephrology," $2^{nd}$ ed., pp. 404–439, eds., Davidson, A.M., et al., Oxford Univ. Press (1998).

Ueda, N., et al., "*In Vivo* Evidence for a Role of Reactive Oxygen Metabolites in Glomerular Disease", *Kidney: A Current Survey of World Literature*, 6:143–146 (1997).

Boyce, N.W., et al., "Hydroxyl radical mediation of immune renal injury by desferrioxamine", *Kidney International*, 30:813–817 (1986).

Baliga, R., et al., "Kidney Iron Status in Passive Heymann Nephritis and the Effect of an Iron–Deficient Diet", *J Am Soc Nephrol*, 7(8):1183–1188 (1996).

Shah, S.V., et al., "Evidence suggesting a role for hydroxyl radical in passive Heymann nephritis in rats", *The American Physiological Society*, F337–F344(1988).

Thakur, V., et al., "Evidence suggesting a role for hydroxyl radical in puromycin aminonucleoside–induced proteinuria", *Kidney International*, 34:494–499 (1988).

Nankivell, B.J., et al., "The Role of Tubular Iron Accumulation in the Remnant Kidney", *J Am Soc Nephrol*, 4(8):1598–1607 (1994).

Alfrey, A.C., et al., "Role of iron in the tubulo–interstitial injury in nephrotoxic serum nephritis", *Kidney International*, 36:753–759 (1989).

El Nahas, A.M., "Mechanisms of experimental and clinical renal scarring" In: "Oxford Textbook of Clinical Nephrology", $2^{nd}$ ed., pp. 1749–1788, eds., Davidson, A.M., et al., Oxford Univ. Press (1998).

Howard R.L., et al., "Urinary albumin, transferrin and iron excretion in diabetic patients", *International Society of Nephrology*, 40:923–926 (1991).

Olivieri, N.F., et al., "Iron–Chelation Therapy with Oral Deferiprone in Patients with Thalassemia Major", *The New England Journal of Medicine*, 918–922 (1995).

Alfrey A.C., "Toxicity of tubule fluid iron in the nephrotic syndrome", *American Journal of Physiology*, 263(4):F637–F641 (1992).

Wu,Z–L, et al., "Iron Loading Enhances Susceptibility to Renal Ischemia in Rats," *Renal Failure* 16(4):471–480 (1994).

Baliga, R. et al., "In Vitro and In Vivo Evidence Suggesting a Role for Iron in Cistaplin–induced Nephrotoxicity," *Kidney International* 53(2):394–401 (Feb. 1998).

Harris, D. et al., "Mitrochondrial Function in Rat Renal Cortex in Response to Proteinuria and Iron," *Clinical and Experimental Pharmacology and Physiology* 24:916–922 (Dec. 1997).

\* cited by examiner

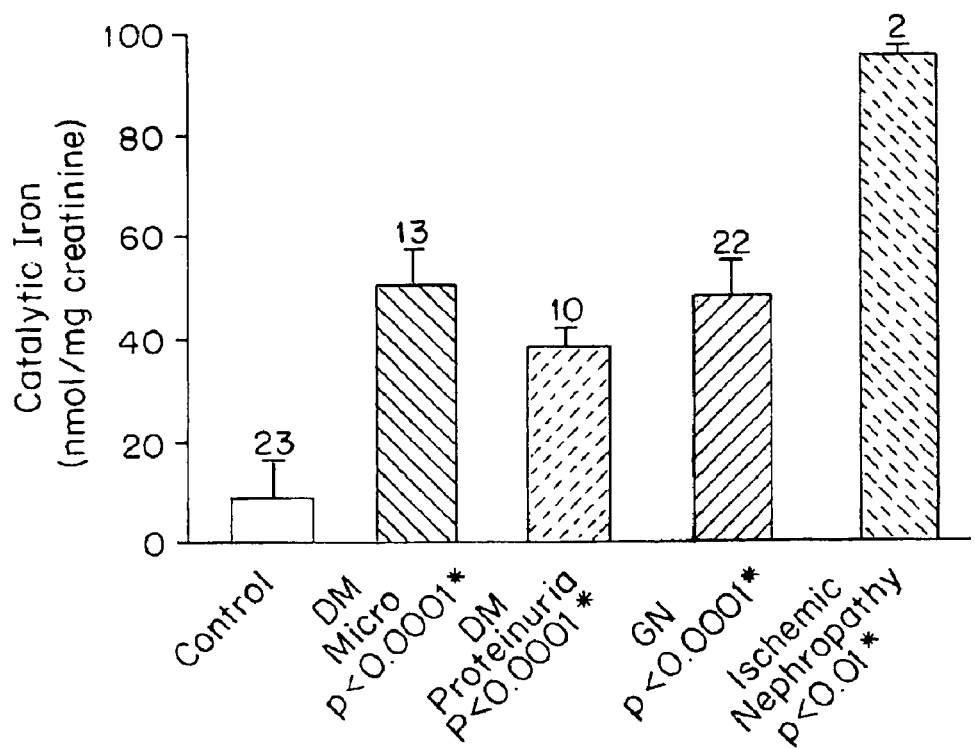

DIAGNOSIS AND TREATMENT OF HUMAN KIDNEY DISEASES

RELATED APPLICATIONS

This application is a divisional of U.S. application Ser. No. 09/553,496 filed Apr. 20, 2000 which claims the benefit of U.S. Provisional Applications Ser. Nos. 60/130,903 and 60/130,908, both filed Apr. 23, 1999, the entire teachings of both of which are incorporated herein by reference.

BACKGROUND OF THE INVENTION

Kidney disease can be progressive, leading to end-stage renal disease and, ultimately, death. End-stage renal disease affects approximately 650,000 human patients each year worldwide and treatment costs have been estimated to be about twenty billion dollars (Klahr, S., Contrib. Nephrol. 118:1–5 (1996)).

Current methods to diagnose kidney disease and, in particular, progressive kidney disease, include monitoring urine for elevated protein levels and conducting renal biopsies. Available treatments for kidney disease, specifically progressive kidney disease, include the use of steroids, alkylating agents and cyclosporine (de Mattos, A. M. et al., pages 861–885, In: "Immunologic Renal Diseases," eds. Neilson, E. G. et al., Lippincott-Raven Publishers, Philadelphia, Pa. (1997)). The above mentioned diagnostic methods often are inadequate since significant damage to the kidney can occur prior to diagnosis. Likewise, the above mentioned treatments frequently are unsuccessful in halting the progression of kidney disease and, therefore, unsatisfactory, since they often are accompanied by adverse side effects, such as cellular and systemic toxicity.

Although animal models have been used to study some kidney diseases, animal models suffer from a number of limitations when extended to human kidney disease diagnosis and treatment. For example, animal models of kidney disease do not necessarily depict kidney disease in humans and the administration of steroids, although reasonably effective in the treatment of kidney disease in experimental animal models, are relatively ineffective in the treatment of kidney disease in humans (Siegel, N. J. et al., Kidney Int. 25:906–911 (1984); Cronin, R. E., et al., Am. J. Physiol. 248:F332–F339 (1985); Cronin, R. E., et al., Am. J. Physiol. 251:F408–F416 (1986); Seiken, G. et al., Kidney Int. 45:1622–1627 (1994); Shaw, S. G. et al., J. Clin. Invest. 80:1232–1237 (1987); Allgren, R. L. et al., N. Eng. J. Med. 336:828–834 (1997); Paller, M. S., Sem. Nephrol. 18:482–489 (1998); Savill, J., et al., In: "Oxford Textbook of Clinical Nephrology", eds. Davison, A. M., et al., Oxford Medical Publications, page 403–439 (1998); Hirschberg, R. et al., Kidney Int. 55:2423–2432 (1999)). Thus, animal model systems generally can not be used to define and identify methods which halt the progression, reduce the severity, treat, or diagnose progressive kidney disease in humans. Thus, there is a need to develop new, improved and effective methods of reducing the severity, diagnosing and treating kidney disease in humans.

SUMMARY OF THE INVENTION

The present invention relates to methods of diagnosing and treating kidney disease in a human. In particular, the invention relates to methods of treating progressive kidney diseases.

In one embodiment, the method includes diagnosing a kidney disease in a human comprising the step of measuring catalytic iron in a urine sample. In a preferred embodiment, the catalytic iron is measured in relation to a reference protein. In a particularly preferred embodiment, the reference protein is urinary creatinine.

In another embodiment, the invention relates to a method of treating a kidney disease in a human comprising measuring catalytic iron content in a urine sample obtained from the human and comparing catalytic iron content in the urine sample with catalytic iron content in a control sample. A catalytic iron content in the urine sample above catalytic iron content in the control sample is indicative of kidney disease.

In yet another embodiment, the invention includes a method of treating a kidney disease in a human, wherein the human has a catalytic iron content in urine greater than about 15 nmol/mg of a reference protein comprising administering an iron chelator to the human.

In an additional embodiment, the invention includes a method of treating a kidney disease in a human comprising administering a dose of an iron chelator to a human having catalytic iron content in urine exceeding that of a control sample and obtaining a first urine sample from the human. The catalytic iron content in the first urine sample is measured and compared to the catalytic iron content in the catalytic iron content in the control sample.

The method can further include administering at least one subsequent dose of the iron chelator. The amount of the subsequent dose is determined by comparison of the measured catalytic iron content in the urine sample to the catalytic iron content in the control sample.

In another embodiment, the method further includes obtaining at least one subsequent urine sample and measuring catalytic iron content in the subsequent urine sample. The catalytic iron content in the subsequent urine sample is compared to the catalytic iron content in the first urine sample, the control sample or both.

Yet another embodiment of the invention includes determining progression of kidney disease in a human. Catalytic iron content in a first urine sample and at least one additional urine sample obtained from the human is measured. Catalytic iron content in the additional urine sample is compared with catalytic iron content in the first urine sample. An elevation in catalytic iron content in an additional urine sample above catalytic iron content in the first urine sample is indicative of the progression of the kidney disease in the human.

In still another embodiment, the invention relates to a method of evaluating the effectiveness of administering an iron chelator to treat a human suffering from a progressive kidney disease. Catalytic iron content in a first urine sample obtained from the human is compared with catalytic iron content of a subsequent urine sample obtained from the human. The subsequent urine sample is obtained after obtaining the first urine sample and after the administration of the iron chelator. A comparison of the catalytic iron content in the subsequent urine sample and the first urine sample is indicative of the effectiveness of the administration of the iron chelator to alleviate progression of the kidney disease.

In another embodiment, the invention relates to a method of identifying a human suffering from a progressive kidney disease who will benefit from treatment of the progressive kidney disease with the iron chelator. Catalytic iron content in a urine sample obtained from the human is measured. A catalytic iron content in the urine sample greater than about 15 nmol/mg of a reference protein identifies a human suffering from a progressive kidney disease who will benefit from treatment of the progressive kidney disease with the iron chelator.

In yet another embodiment, the invention relates to a method of treating microalbuminuria in a human comprising administering a dose of an iron chelator to a human suffering from microalbuminuria having a catalytic iron content in urine exceeding a control sample. A first urine sample is obtained from the human and catalytic iron content measured in the first urine sample. The catalytic iron content in the first urine sample is compared with the catalytic iron content in the control sample.

The invention described herein provides methods for diagnosing, treating, halting the progression and reducing the severity of kidney disease in a human. Advantages of the claimed invention include, for example, treatment of progressive kidney disease in a human in a manner which has not been described in an animal model, nor could not be predicted from existing animal models of kidney disease. The methods of the invention can treat progressive kidney diseases in humans without significant side effects. The methods of the invention provide an effective manner to treat kidney disease and, ultimately, prevent end-stage renal disease.

Thus, treatment of humans who have a catalytic iron content in the urine above a control level with iron chelators, can halt, reverse, or reduce the severity of the progression of kidney disease, thereby increasing quality of life and life expectancy.

BRIEF DESCRIPTION OF THE FIGURES

The FIGURE represents the catalytic iron content (nmol/mg urinary creatinine) in urine obtained from humans with no kidney disease (control), with diabetic microalbuminuria (DM Micro), diabetic (DM) proteinuria, glomerulonephritis (GN) and ischemic nephrophathy.

DETAILED DESCRIPTION OF THE INVENTION

The features and other details of the invention, either as steps of the invention or as combinations of parts of the invention, will now be more particularly described and pointed out in the claims. It will be understood that the particular embodiments of the invention are shown by way of illustration and not as limitations of the invention. The principle features of this invention can be employed in various embodiments without departing from the scope of the invention.

The present invention relates to the discovery that catalytic iron in urine of a human can be an indicator of the existence of kidney disease. The invention further relates to the discovery that the administration of an iron chelator decreases protein content in urine of humans suffering from kidney diseases. In particular, the iron chelator deferiprone has been found to decrease protein content and serum creatinine, both indices of kidney damage, in urine obtained from humans suffering from progressive kidney disease.

"Kidney disease" generally refers to a disorder of at least one kidney in a human that compromises the function of the kidney (e.g., to prevent leakage of protein, to prevent excretion of nitrogenous waste). The kidney disease can result from a primary pathology of the kidney (e.g., injury to the glomerulus or tubule) or another organ (e.g., pancreas) which adversely affects the ability of the kidney to perform biological functions (e.g., retain protein). Thus, kidney disease in the human can be the direct or indirect effect of disease. Examples of a kidney disease as a result or consequence of an indirect effect on the kidneys is kidney disease as a consequence of diabetes or systemic lupus. The term kidney disease is used interchangeably with the phrase "diseases of the kidney." The kidney disease can be, for example, a result or a consequence of any change, damage, or trauma to the glomerulus, tubules or interstitial tissue in either the renal cortex or renal medulla of the kidney.

In a preferred embodiment of the invention, the kidney disease is a progressive kidney disease. "Progressive kidney disease" as used herein refers to any disease of the kidney that over time (e.g., days, weeks, months, years) leads to a loss of renal function. "Renal function" generally refers to a physiological property of the kidney, such as the ability to retain protein thereby preventing proteinuria (e.g., urinary creatinine, the excretion of protein in an amount greater than about 0.15 g/24 hours). Renal function can be assessed, for example, by glomerular filtration rate (e.g., creatinine clearance), excretion of protein in urine, blood urea nitrogen, serum or plasma creatinine, or any combination thereof.

Glomerular filtration rate is an indicia of renal function which generally refers to the renal (also referred to herein as kidney) excretory capacity. Indices to assess glomerular filtration include, for example, creatinine clearance and inulin clearance. Exemplary descriptions and discussions of techniques to assess renal function, including glomerular filtration rate (e.g., creatinine clearance) are found, for example, in Larsen, K. *Clin. Chem. Acta.* 41:209–217 (1972); Talke, H. et al., *Klin, Wscr* 41:174 (1965); Fujita, Y. et al., *Bunseki Kgaku* 32:379–386 (1983); Rolin, H. A. III, et al., In: "The Principles and Practice of Nephrology", 2nd ed., Jacobson, H. R., et al., Mosby-Year Book, Inc., St. Louis, Mo., page 8–13 (1995); Carlson, J. A., et al., In: "Diseases of the Kidney", 5th Ed., Schrier, R. W. et al., eds., Little, Brown and Co., Inc., Boston, Mass., pages 361–405 (1993), the teachings of all of which are hereby incorporated by reference in their entirety. For example, endogenous creatinine clearance can be determined as follows:

$$Cr = Ucr\ V/PCr$$

where Cr=clearance of creatinine (ml/min); Ucr=urine creatinine (mg/dl), V=volume of urine (ml/min—for 24-hr volume: divide by 1400, and PCr=plasma creatinine (mg/dl).

A progressive kidney disease treated by the methods described herein includes any kidney disease that can, ultimately, lead to end-stage renal disease. A progressive kidney disease of the invention is not a disease of the kidney that results from exogenous iron overload as a result of, for example, repeated blood transfusions in diseases such as thalassemia or sickle cell anemia. The progressive kidney diseases that can be diagnosed or treated by the methods of the invention can be, for example, associated with endogenous iron deposit in the kidney (e.g., glomerulus, tubules). The endogenous iron can be released, for example, from ferritin, mitochondria or cytochrome P450 in the human.

In a more preferred embodiment, the kidney disease is a progressive glomerular kidney disease. Progressive glomerular kidney diseases that are particularly suitable for treatment by the method of the invention include, for example, diabetic nephropathy (e.g., as a consequence of Type I or Type II diabetes or systemic lupus), primary glomerulonephritis (e.g., membranous nephropathy, focal segmental glomerulosclerosis, membranoproliferative glomerulonephritis, diffuse proliferative glomerulonephritis, membranous focal segmental glomerulosclerosis) and secondary glomerulonephritis (e.g., diabetic nephropathy, ischemic nephropathy).

A kidney disease can be diagnosed in a human by the method of the invention by measuring the catalytic iron in urine of the human. A human is also referred to herein as a patient or an individual. In a preferred embodiment, a human can be diagnosed with a kidney disease when catalytic iron content in urine is greater than about 15 nmol/mg of a reference protein.

"Catalytic iron" refers to $Fe^{2+}$. Catalytic iron is capable of catalyzing free radical reactions. Iron in the $Fe^{2+}$ state can catalyze the Haber-Weiss reaction, which reduces hydrogen peroxide and promotes formation of hydroxyl radicals. The Haber-Weiss reaction is illustrated below:

$$O_2^- + Fe^{3+} \rightarrow O_2 + Fe^{2+}$$
$$\underline{Fe^{2+} + H_2O_2 \rightarrow Fe^{3+} + OH\bullet + OH^-}$$
$$O_2^- + H_2O_2 \rightarrow O_2 + OH\bullet + OH^-$$

It is also envisioned that catalytic iron can result in the formation of hydroxyl radicals in reactions other than the Haber-Weiss reaction.

Methods to determine the catalytic iron content are known (see, for example, Gutteridge, J. M. C. et al., *Biochem J.* 199:263–265 (1981); Yergey, A. L. *J. Nutrition* 126:355S–361S (1996); Iancu, T. C. et al., *Biometals* 9:57–65 (1996); Artiss, J. D. et al., *Clin. Biochem.* 14:311–315 (1981); Smith, F. E. et al., *Clin. Biochem.* 17:306–310 (1984); Artiss, J. D., et al., *Microchem. J.* 28:275–284 (1983), the teachings of all of which are hereby incorporated by reference in their entirety) and as described in the exemplification. The methods include spectrophotometric, mass spectrometry (e.g., thermal ionization mass spectrometry, laser microprobe mass analysis, inductively coupled plasma mass spectrometry, atom bombardment-secondary ion mass spectrometry). Catalytic iron content is also referred to as an amount, level or concentration of catalytic iron.

In a preferred embodiment, the catalytic iron content is measured in relation to a reference protein in the urine sample. The phrase "in relation to a reference protein" as used herein refers to expressing catalytic iron content in urine as a unit of measurement (e.g., nanomoles) per a concentration of a protein (e.g., milligrams) in the urine. Catalytic iron can be expressed, for example, as nanomoles (nmoles) of catalytic iron per milligram (mg) of protein in urine. In a preferred embodiment, the reference protein is urinary creatinine.

Additionally, or alternatively, catalytic iron content is measured in relation to glomerular filtration rate, in particular creatinine clearance as described above.

Preferably, catalytic iron content is measured in a urine sample from a human prior to the onset of clinical symptoms (also referred to herein as clinical signs of kidney disease) of kidney disease (e.g., proteinuria, increase blood urea nitrogen, increase serum creatinine). Additionally, or alternatively, catalytic iron content is measured in a urine sample obtained from the human after the onset of clinical symptoms of kidney disease (e.g., proteinuria). Catalytic iron is measured in humans afflicted with a kidney disease and compared to humans not afflicted with a kidney disease (See Tables 1 and 2).

An "iron chelator" refers to any molecule capable of interacting with iron, either $Fe^{3+}$ or $Fe^{2+}$, to prevent the formation of catalytic iron from $Fe^{3+}$ or to prevent, inhibit or interfere with iron ($Fe^{3+}$ or $Fe^{2+}$) interacting, effecting or participating in the Haber-Weiss reaction or any other reaction which can generate hydroxyl radicals. The interaction between the iron chelator and iron, either $Fe^{3+}$, $Fe^{2+}$, or both, can be, for example, a binding interaction, an interaction as a result of steric hindrance or any reciprocal effect between iron and the iron chelator. The iron chelator can, for example, prevent the conversion of $Fe^{3+}$ to $Fe^{2+}$, thereby indirectly preventing the reduction of hydrogen peroxide and formation of hydroxyl radicals in the Haber-Weiss reaction. Alternatively, or additionally, the iron chelator can interact directly with $Fe^{2+}$ to prevent hydroxyl radical formation in, for example, the Haber-Weiss reaction.

The iron chelator can be a peptide comprising natural or nonnatural (e.g., amino acids not found in nature) amino acids, polyethylene glycol carbamates, lipophilic or nonlipophilic polyaminocarboxylic acids, polyanionic amines or substituted polyaza compounds. In a preferred embodiment, the iron chelator is deferiprone (1,2-dimethyl-3-hydroxypyrid-4-one)L1. Iron chelators are commercially available or can be synthesized or purified from biological sources using routine procedures. Exemplary descriptions and discussions of iron chelators are found in several references, for example, U.S. Pat. No. 5,047,421 (1991); U.S. Pat. No. 5,424,057 (1995); U.S. Pat. No. 5,721,209 (1998); U.S. Pat. No. 5,811,127 (1998); Olivieri, N. F. et al., *New Eng. J. Med.* 332:918–922 (1995); Boyce, N. W. et al., *Kidney International.* 30:813–817 (1986); Kontoghiorghes, G. J. *Indian J. Peditr.* 60:485–507 (1993); Hershko, C. et al., *Brit. J. Haematology* 101:399–406 (1998); Lowther, N. et al., *Pharmac. Res.* 16:434 (1999), the teachings of all of which are hereby incorporated by reference in their entirety.

An "amount effective," when referring to the amount of iron chelator is defined as that amount (also referred to herein as dose) of iron chelator that, when administered to a human afflicted with a kidney disease, is sufficient for therapeutic efficacy (e.g., an amount sufficient to reduce the catalytic iron content in urine, total protein content in urine, blood urea nitrogen, or creatinine in a blood sample obtained from a human with a progressive kidney disease). An effective amount of an iron chelator also refers to an amount of iron chelator that when administered to the human prevents a further or additional increase in urinary catalytic iron content compared to the catalytic iron content measured in urine prior to treatment or during treatment with the iron chelator. Catalytic iron can be measured in urine of humans undergoing treatment with iron chelator before, during or after the administration of the iron chelator.

In one embodiment, the iron chelator is administered in a single dose. In another embodiment, the iron chelator is administered in multiple doses. In a preferred embodiment, the iron chelator is administered orally at a dose in a range between about 20 mg/kg body of the human and about 150 mg/kg body weight of the human. In a particularly preferred embodiment, the iron chelator is administered three times a day at a dose in a range of between about 20 mg/kg body of the human and about 150 mg/kg body weight of the human for at least 2–6 months.

Another aspect of the invention relates to measuring protein content in urine of a human afflicted with a progressive kidney disease undergoing treatment of the kidney disease with an iron chelator. A measure of protein content can be total protein in the urine (also referred to herein as total protein content). Protein content in urine of the human afflicted with the kidney disease can be measured at one or more time points before, during or after the administration of the iron chelator.

Typically, protein content in urine is determined using routine assays well-known to one of skill in the art. Suitable methods include dipstick, immunoprecipitation, turbidimetric (e.g., sulphosaliclic acid, tricholoracetic, benzethonium chloride) assays, dye-binding (e.g., Coomassie Blue, Ponceau) assays, Biuret (e.g., precipitation with Tsuchiya reagent) assays and Folin-Lowry assays. ("Oxford Textbook of Clinical Nephrology" eds. Davison, A. M., et al., 2nd edition, Oxford University Press, New York, N.Y. (1998); "Primer on Kidney Diseases" ed., Greenberg, A., 2nd edition, Academic Press, New York, N.Y. (1998), the teachings of all of which are hereby incorporated by reference in their entirety).

In another embodiment, creatinine, blood urea nitrogen, or both are measured in a blood sample obtained from the human at one or more time points before, during or after the administration of the iron chelator to a human afflicted with a kidney disease. The blood sample can be an arterial blood sample or venous blood sample. The blood sample can be a serum or plasma blood sample. Methods to obtain blood samples and process the blood sample to determine blood urea nitrogen content and creatinine content are well known to one of skill in the art. (See, for example, Karlinsky, M. L. et al., *Kidney Int.* 17:293–302 (1980); Tomford, R. C. et al., *J. Clin. Invest.* 68:655–664 (1981); Baliga, R. et al., *Biochem J.* 291:901–905 (1993), the teachings of all of which are incorporated herein by reference in their entirety).

Blood urea nitrogen, urinary protein content or serum creatinine content in a human afflicted with a kidney disease can increase in the human as the kidney disease progresses. Likewise, blood urea nitrogen, total urinary protein content and serum creatinine content in a human afflicted with a kidney disease can decrease or stabilize (e.g., remain the same, essentially constant) when the progression of a kidney disease is halted or prevented by the administration of iron chelators using the methods of the invention.

In a preferred embodiment, the iron chelator is administered to the human with a kidney disease in an amount effective to lower total protein content in urine, blood urea nitrogen or creatinine content in a blood sample of the human to about that of a control level.

In another embodiment, the iron chelator is administered to the human with a kidney disease in an amount effective to prevent any further increase in total protein content in urine, blood urea nitrogen and creatinine content in a blood sample of the human compared to an amount of catalytic iron prior to treatment with the iron chelator (also referred to herein as a pretreatment amount of urinary catalytic iron).

In yet another embodiment, the iron chelator is administered to the human with a kidney disease in an amount effective to prevent an increase in total protein content in urine, blood urea nitrogen and creatinine in a blood sample of the human to a level above a control level.

In particular, the invention relates to a method of treating a kidney disease in a human, comprising administering a dose of an iron chelator (e.g., in a range between about 20 mg iron chelator/kg body weight and about 150 mg iron chelator/kg body weight) to a human having a catalytic iron content in urine exceeding that of a catalytic iron content in a control sample (e.g., above about 15 nmol catalytic iron/ mg of a reference protein). The dose which the human is initially treated with is also referred to as an "initial dose."

In one embodiment, a urine sample is obtained from a human before the administration of the iron chelator (also referred to herein as a pretreatment urine sample). In another embodiment, a urine sample is obtained after the administration of the iron chelator. Thus, a urine sample can be obtained from the human before, during or after the human is administered the iron chelator and catalytic iron content measured.

In a preferred embodiment, the iron chelator (e.g., deferiprone) is administered to a human with a catalytic iron content in a urine sample in an amount greater than about 15 nmol/mg of a reference protein (e.g., urinary creatinine) in a dose in a range of between about 20 mg/kg body weight and about 150 mg/kg body weight of the human.

As defined herein, "control sample" means a level (also referred to herein as amount or content) of the parameter of interest (e.g., catalytic iron content in urine, protein content in urine, blood urea nitrogen in a blood sample, creatinine in a blood sample) in a human not afflicted with a kidney disease, matched, as necessary, for variables, such as age, sex, ethnicity and health history, with the human to be treated. A control sample can also be the expected level of the parameter of interest in a human. The "expected level" of the parameter of interest in a human treated by the methods of the invention can be a level normally observed in a human not afflicted with the kidney disease, or can be higher than a human not afflicted with the kidney disease yet below the level in a human with a kidney disease. An expected level can also be any level of the parameter of interest that is below pretreatment levels or lower than a level expected during progression of a kidney disease in a human not undergoing treatment by the methods defined herein. A "target level" of the parameter of interest can be selected for a human afflicted with a kidney disease based on a level of the parameter of interest (e.g., catalytic iron content in the urine) of a human before that human developed a kidney disease, or in comparison to levels observed in a human not exhibiting a kidney disease. In a preferred embodiment, a control sample has a catalytic iron content of about 15 nmol/mg of a reference protein (e.g., creatinine).

After administration of the iron chelator, the catalytic iron content in the human is measured in a first urine sample. A "first urine sample," when referring to methods of treating the progressive kidney disease, refers to a urine sample obtained from the human at any time after the administration of the iron chelator. The first urine sample can be obtained, for example, days, weeks, months, or years after the administration of the iron chelator. The catalytic iron content in a urine sample (e.g., first urine sample) is compared to the catalytic iron content in the control sample. The catalytic iron content in the first urine sample can also be compared to the catalytic iron content in a urine sample obtained from the human prior to or after administering the initial dose of the iron chelator.

The method can further include administering a subsequent dose of the iron chelator to the human. The amount of the subsequent dose administered is determined by comparing the catalytic iron in the first urine sample with the catalytic iron content in the control sample.

The method can further include obtaining as least one subsequent urine sample from the human. A "subsequent urine sample" is any urine sample obtained from the human at any time after the first urine sample. One or more subsequent urine samples can be obtained from the human. More than one subsequent urine sample can be obtained in a day or over several days, months or years.

The catalytic iron content in the subsequent urine sample of the human is compared with the catalytic iron content in the first urine sample, the control sample, or both. The dose of the iron chelator administered to the human can be adjusted (e.g., increased) until the catalytic iron content in the urine of the human is about that of the control sample or until the catalytic iron content in the subsequent urine sample is essentially constant. The adjusted dose is also referred to as a "subsequent dose." For example, if the human was administered about 75 mg/kg body weight dose of iron chelator and the catalytic iron content in a subsequent urine sample was about 35 nmol/mg of a reference protein compared to about 55 nmol/mg of a reference sample in the urine sample or first urine sample, the subsequent dose of iron chelator could be adjusted to below about 75 mg/kg body weight.

In another embodiment of the invention, the subsequent dose of the iron chelator is administered until the catalytic iron in a subsequent urine sample is about that of the control or essentially constant. "Essentially constant" (also referred to herein as "an essentially constant value" or stabilized) refers to a catalytic iron content in the urine that remains about the same value over time (e.g., days, weeks, months, or years).

In a preferred embodiment, when the catalytic iron content in urine is about that of a control sample or essentially constant, the dose of iron chelator in at least two subsequent doses differs by about 10 mg/kg of body weight of the human. After a 10 mg/kg increment adjustment, the catalytic iron content in one or more subsequent urine samples can be measured, compared to the control or an essentially constant value and the dose of iron chelator adjusted (e.g., increased) if the catalytic iron content in the subsequent urine sample is above a control sample or the essentially constant value. For example, if the catalytic iron content in a subsequent urine sample of a human on a maintenance dose of the iron chelator is greater than the control sample (e.g., about 15 nmol/mg of a reference protein) the dose of iron chelator can be increased to decrease the catalytic iron in the urine of the human afflicted with a kidney disease. Similarly, the dose of iron chelator can be decreased if the catalytic iron content in the subsequent urine sample remains, for example, at a control content or essentially constant.

In yet another embodiment, urinary protein content (e.g., total protein content) in a urine sample (e.g., before or after treatment with the iron chelator) and at least one subsequent urine sample is measured. The urinary protein content in the subsequent urine sample is determined and compared to the protein content in a urine sample obtained before or after iron chelator treatment, a control sample or both. Urinary protein content in a subsequent urine sample can be compared to a control sample to determine the progress of treatment, the need for further treatment (e.g., number or duration of doses) or the need to adjust the dose (e.g., mg/kg body weight) of iron chelator being administered to the human.

"Adjusting the dose" of the iron chelator (also referred to herein as a subsequent dose of iron chelator) refers to any change or alteration (e.g., increase or decrease) in the amount of iron chelator in the initial dose. A change in the amount of iron chelator can be, for example, an increase or decrease in the frequency (e.g., times per day, number of days, number of months, number of years) of administration of the iron chelator. Additionally, or alternatively, a change in the amount of iron chelator can be an increase or decrease in the dose (e.g., milligrams of iron chelator per kilogram body weight of the human) of iron chelator administered to the human.

In another embodiment of the invention, creatinine content or blood urea nitrogen content in a blood sample obtained from the human is measured at one or more points before, during or after administration of the iron chelator to a human afflicted with a kidney disease, and who has a catalytic iron content in urine greater than a control sample.

Additionally indices of reducing the severity of the progressive kidney disease can be a decrease in the expected, rate at which, for example, blood urea nitrogen, serum creatinine increases, glomerular filtration rate declines, or the onset of end-stage renal disease is delayed. A decline in glomerular filtration rate can be assessed, for example, by an increase in total urinary protein.

A blood sample obtained from the human before administration of an iron chelator is referred to as a "pretreatment blood sample." A blood sample obtained from the human after or during the administration of the iron chelator is also referred to as a "subsequent blood sample." The blood urea nitrogen content and creatinine content in at least one subsequent blood sample is compared with the blood urea nitrogen content and creatinine content in at least one pretreatment blood sample or a control sample. Similarly, the blood urea nitrogen content and creatinine content is compared in at least one subsequent blood sample obtained from the human at different times following the administration and during the course of iron chelator treatment.

The dose of iron chelator can be adjusted depending upon protein content in urine, blood urea nitrogen, creatinine content in the subsequent blood sample, or any combination thereof. For example, a decline (also referred to herein as a decrease) in urinary protein, blood urea nitrogen or creatinine content in a subsequent urine or blood sample compared to a pretreatment sample or a control sample is indicative that the kidney disease is being treated by the iron chelator and the dose of iron chelator could be decreased.

In another embodiment of the invention, a kidney disease in a human is diagnosed. Catalytic iron content is measured in a urine sample obtained from the human and compared with catalytic iron content in a control sample. In this embodiment, catalytic iron content in the urine sample obtained from the human above the catalytic iron content in the control sample is indicative of kidney disease.

In another embodiment, the invention relates to a method of reducing the severity of a progressive kidney disease in a human having a catalytic iron content in a urine sample greater than about 15 nmol/mg of a reference protein. The human afflicted with the progressive kidney disease (e.g., diabetic nephropathy, primary glomerulonephritis, secondary glomerulonephritis) is administered an iron chelator. The iron chelator decreases catalytic iron content in urine obtained from the human thereby reducing the severity of the progressive kidney disease.

The phrase "reducing the severity" (also referred to herein as a reduction in the severity) when referring to a progressive kidney disease means any diminution, amelioration or decrease in progressive damage to the kidney that compromises the function of the kidney. Well-recognized indices to assess function of the kidney can be employed to determine a reduction in the severity of the kidney disease. These indices can include, for example, a reduction in protein content in urine, a reduction in blood urea nitrogen, a reduction in serum or plasma creatinine, an increase in glomerular filtration rate, a delay in the onset of end-stage renal disease, or any combination thereof, compared to a sample obtained from the human prior to administering the iron chelator, or a control sample.

A reduction in the severity of the kidney disease can result, for example, from an amelioration of a primary pathology of the kidney (e.g., injury to the glomerulus or tubule) or another organ (e.g., pancreas) which had adversely affected the ability of the kidney to perform biological functions (e.g., retain protein). Thus, a reduction in the severity of the kidney disease in the human can be the direct or indirect effect of a reduction of the kidney disease.

Another embodiment of the invention is a method of determining the progression of a kidney disease in a human comprising measuring catalytic iron in one or more urine samples obtained from the human. An increase in the catalytic iron content in a urine sample from the human over time (e.g., weeks, months, years) is indicative of the progression of the kidney disease. The catalytic iron content in urine can be measured relative to a reference protein (e.g., creatinine).

"Progression of a kidney disease" refers to an augmentation or increase in the disease of the kidney. Progression of a kidney disease can include, for example, continued or additional damage to a segment of the kidney (e.g., nephron, tubule, interstitium) that was not damaged when the human was initially afflicted or diagnosed with the kidney disease. For example, the human could have no glomerular damage or damage only to the glomerulus resulting in a kidney disease which, over time, leads to increased damage only to the glomerulus or results in tubular damage as the kidney disease progresses. As the kidney disease progresses in the human, the catalytic iron content in urine can increase above a level prior to additional damage to the kidney or in comparison to a human not affected with a progressive kidney disease. Catalytic iron content in urine obtained from the human with progressive kidney disease can be determined and compared to urinary catalytic iron content in another, different human with various stages of progressive kidney disease to discern the progression of the kidney disease.

Progression of the kidney disease can also be monitored, for example, by measuring protein content, in addition to catalytic iron content, in urine of the human afflicted with the kidney disease. As the kidney disease progresses, the protein content in the urine can increase. Additionally, progression of the kidney disease in the human can be assessed by measuring the blood urea nitrogen content or creatinine content in a blood sample obtained from the human over time. An increase in the blood urea nitrogen content or creatinine content over time in the human is also indicative of the progression of the kidney disease in the human. Similarly, a decline in glomerular filtration as assessed, for example, by creatinine clearance as described above can also be used in conjunction with urinary catalytic iron content as indicative of progression of the kidney disease.

In another embodiment, the invention relates to a method of determining the progression of kidney disease in a human comprising measuring catalytic iron content in a first urine sample and in at least one additional urine sample obtained from the human. When determining the progression of a kidney disease, a "first urine sample" refers to an initial sample of urine obtained from the human at anytime prior to determining the progression of the kidney disease. An "additional urine sample" refers to a urine sample obtained from the human at any time after the first urine sample.

The catalytic iron content in the additional urine sample is compared to the catalytic iron content in at least one additional urine sample. An elevation in the catalytic iron in an additional urine sample compared to a first urine sample is indicative of progression of the kidney disease. Likewise, a reduction in the catalytic iron in an additional urine sample compared to the first urine sample is indicative that the kidney disease is not progressing or is being reduced in severity.

The method of determining the progression of kidney disease in a human can further include measuring protein content in the first urine sample and at least one additional urine sample and creatinine content in a first blood sample and at least one additional blood sample obtained from the human afflicted with the kidney disease. A "first blood sample" refers to an initial blood sample obtained from the human at anytime prior to determining the progression of the kidney disease. An "additional blood sample" refers to a blood sample obtained from the human at anytime after the first blood sample.

The protein content in an additional urine sample can be compared to the protein content in the first urine sample and the creatinine content in the additional blood sample can be compared to the first blood sample. An elevation in protein content in the additional urine sample above protein content in the first urine sample and/or an elevation in creatinine content in the additional blood sample above the creatinine content in the first blood sample can be indicative of the progression of the kidney disease in the human. Likewise, a decrease in protein content in the additional urine sample below the protein content in the first urine sample and/or an decrease in creatinine content in the additional blood sample below the creatinine content in the first blood sample is indicative that the kidney disease is not progressing in the human. Similarly, an essentially constant protein content in the additional urine sample can indicate that the kidney disease is not progressing.

Additionally the method of determining the progression of kidney disease in the human can further include comparing blood urea nitrogen in additional blood sample compared to a first blood sample. An elevation in blood urea nitrogen content in the additional blood sample above blood urea nitrogen content in the first blood sample is indicative of the progression of the kidney disease in the human. Similarly, a decrease in blood urea nitrogen content or an essentially constant blood urea nitrogen content in the additional blood sample below blood urea nitrogen content in the first blood sample is indicative the kidney disease is not progressing.

In another embodiment of the invention, the effectiveness of treatment with an iron chelator in a human suffering from a kidney disease is evaluated. Catalytic iron content in at least two urine samples are obtained from the human and compared. "Evaluating the effectiveness" refers to assessing the success of treating the human afflicted with a kidney disease, in particular a progressive kidney disease, and especially a progressive glomerular kidney disease with an iron chelator to the extent that the kidney disease is treated (e.g., that the kidney disease does not progress).

The urine samples obtained from the human to evaluate the effectiveness of treatment with the iron chelator includes a pretreatment urine sample obtained from the human at a pretreatment time and at least one subsequent urine sample obtained from the human at least at one subsequent time after the pretreatment sample. A "pretreatment time" refers to anytime prior to the administration of the iron chelator. A "subsequent time" refers to anytime after the administration of the iron chelator.

A decrease in catalytic iron content in the subsequent urine sample to an amount below a catalytic iron content in the pretreatment urine sample is indicative of the effectiveness of treatment of the kidney disease. Evaluation of the effectiveness of treatment with an iron chelator can further include comparing protein content in the pretreatment urine sample and at least one subsequent urine sample. A decrease in protein content in the subsequent urine sample below protein content in the pretreatment urine sample is indicative of the effectiveness of treatment with an iron chelator in a human suffering from a kidney disease.

In yet another embodiment of the invention, evaluation of the effectiveness of treatment with an iron chelator can further include measuring blood urea nitrogen content and creatinine content in a first blood sample and in a subsequent blood sample obtained from the human. The blood urea nitrogen content and creatinine content in the subsequent blood sample is compared with blood urea nitrogen content and creatinine content in the first blood sample. A decrease in blood urea nitrogen content or creatinine content in the subsequent blood sample below blood urea nitrogen content or creatinine content in the first blood sample is indicative of the effectiveness of treatment with an iron chelator in a human suffering from a kidney disease.

Thus, the effectiveness of treatment with an iron chelator can be evaluated by assessing decreases in urinary catalytic content, urinary protein content, blood urea nitrogen content and creatinine content in a blood sample compared to a pretreatment sample or a control sample.

Another embodiment of the invention relates to a method of slowing the progression of a kidney disease in a human having catalytic iron in urine greater than about 15 nmol/mg of a reference protein, comprising administering an iron chelator to the human. The iron chelator can decrease the catalytic iron content in urine obtained from the urine thereby slowing the progression of the kidney disease in the human.

"Slowing the progression" of a kidney disease refers to reducing the rate or speed at which, or degree to which a kidney disease advances or develops. For example, the progression of a kidney disease can be slowed so that additional glomerular damage or damage to the tubules in a kidney that began with glomerular damage does not occur until a time later than similar damage to the kidney in a human afflicted with the kidney disease who is not administered an iron chelator. Thus, slowing the progression of kidney disease also refers to an increase in the amount of time (e.g., days, months, years) it would take to lead to progressive kidney disease and, particularly progressive glomerular kidney disease or, ultimately, end-stage renal disease in a human who was not administered the iron chelator.

A decrease in catalytic iron content after administration of the iron chelator to the human below a catalytic iron content measured before administering the iron chelator can be used as an indice to assess whether the progression of the kidney disease has been slowed. Additionally, or alternatively, other parameters which is indicative of a slowing of the progression of kidney in a human administered an iron chelator can include, for example, decrease in the urinary protein content, blood urea nitrogen or creatinine in a blood sample obtained from the human during or after administration of the iron chelator compared to urinary protein content, blood urea nitrogen or creatinine in a blood sample obtained from the human before administering the iron chelator, or to a level about that of a control sample.

In yet another embodiment, the invention relates to a method of identifying a human suffering from a progressive kidney disease who will benefit from treatment of the progressive kidney disease with an iron chelator. The phrase "who will benefit" refers to a human who has a catalytic iron content in urine greater than about 15 nmol/mg of a reference protein or who can be treated with an iron chelator to, slow the progression of the kidney disease, reduce the severity of the kidney disease or halt the progression of the kidney disease in the human, and particularly, progressive glomerular kidney disease in the human.

To identify a human who will benefit from treatment of a progressive kidney disease, catalytic iron content is measured in a urine sample obtained from the human. A catalytic iron content in the urine sample greater than about 15 nmol/mg of a reference protein identifies a human suffering from a progressive kidney disease who will, or may, benefit from treatment of the progressive kidney disease with the iron chelator.

In still another embodiment, the invention relates to a method of halting the progression of a kidney disease in a human. "Halting" when referring to the progression of a kidney disease in a human refers to stopping, either temporarily or permanently, the progression of the kidney disease in the human. The progression of the kidney disease can be halted, for example, by preventing or diminishing any further damage to any segment of the kidney (e.g., glomerulus, tubules, interstitum) damaged in the human with the progressive kidney disease. Thus, halting of the progression of a kidney disease in a human can be a diminution in glomerular damage or prevention of damage to a segment of the kidney not otherwise damaged in the human with the progressive kidney disease (e.g., preventing tubular damage in a human with glomerular kidney damage).

To halt the progression of a kidney disease in a human, catalytic iron content and protein content is measured in a pretreatment urine sample obtained from the human. An iron chelator is administered to a human having a catalytic iron content in the pretreatment urine sample in an amount greater than about 15 nmol/mg of a reference protein. The iron chelator can be administered in a dose of about 20 mg/kg body weight to about 150 mg/kg body weight of the human. In a preferred embodiment, the iron chelator is deferiprone.

The catalytic iron content and protein content in the human is measured in at least one subsequent urine sample obtained from the human during or after the administration of the iron chelator. The catalytic iron content and protein content in the subsequent urine sample of the human is compared with the catalytic iron content and protein content in a urine sample (e.g., pretreatment urine sample, first urine sample). In one embodiment, the dose of iron chelator administered to the human is adjusted (e.g., increased or decreased compared to the dose initially administered to the human) until the catalytic iron content in a subsequent urine sample of the human is below the control (e.g., 15 nmol/mg of a reference protein). When the protein content in a subsequent urine sample is about twenty five percent (25%) below the protein content in a control sample, the human is maintained on a dose of iron chelator until no further reduction in urinary protein occurs or until the urinary protein is essentially constant (e.g., for 3–4 months). The dose of iron chelator is then reduced by a dose of about 10 mg/kg body weight.

Urinary catalytic iron content is measured in at least one subsequent urine sample following the 10 mg/kg reduction in dose of the iron chelator. The dose of iron chelator can be further reduced by an additional increment for 10 mg/kg body weight as long as the catalytic iron remains essentially constant or at a control level. Urinary catalytic iron content, urinary protein, blood urea nitrogen and creatinine in a blood sample are monitored following each reduction in the dose of iron chelator. If the urinary catalytic iron, total urinary protein, blood urea nitrogen or creatinine in a blood sample increases, the dose of iron chelator can be increased by an increment of 10 mg/kg of body weight of the human. In a preferred embodiment, about every three months the dose of iron chelator is reduced by about 10 mg/kg of body weight. The human can be maintained on a dose of iron chelator about 10 mg/kg body weight higher than the last dose which results in an essentially constant amount of urinary catalytic iron, total urinary protein, blood urea nitrogen or serum creatinine (also referred to herein as a "maintenance dose" of iron chelator).

Catalytic iron content in urine, urinary protein content, blood urea nitrogen or creatinine in blood can be measured while the human is on a maintenance dose of iron chelator and the dose of iron chelator adjusted to, for example, achieve a urinary protein content about that of a control sample. Similarly, if the catalytic iron content in a subsequent urine sample obtained from a human on a maintenance dose of iron chelator is greater than about 15 nmol/mg of a reference protein, the dose of iron chelator can be increased (e.g., to about 20–150 mg/kg of body weight).

The dose of iron chelator can be further increased if the catalytic iron content in the urine sample obtained from the human continues to rise following an adjustment in the dose of iron chelator above the maintenance dose. Similarly, the dose of iron chelator can be decreased if the catalytic iron content in the urine sample obtained from the human decreases following an increase in the dose of iron chelator compared to the maintenance dose. The need to further adjust the dose of iron chelator can be determined by monitoring catalytic iron content in urine, protein content in urine, blood urea nitrogen, creatinine in a blood sample, or any combination thereof.

The invention further relates to the use of iron chelators to diagnose and treat humans exhibiting microalbuminuria. In a preferred embodiment, the iron chelator is deferiprone.

The term "microalbuminuria" refers to any disease, disorder, ailment or state of health where urinary albumin is excreted at a rate of about 20–200 µg/minute or about 30–300 mg/24 hours. (see, for example, Abbott, K. C., et al., *Arch. Internal Med.* 154:146–153 (1994), the teachings of which are incorporated herein by reference in their entirety). Methods to detect and diagnose microalbuminuria are well known to one of skill in the art and include radioimmunoassays, immunoassays with latex bodies, fluoroimmunoassays, enzyme immunoassays, agglutination inhibition, immunoturbidimetry, immunonephelometry and radial immunodiffusion assays. (Keen, H. et al., *Lancet* 2:913–916 (1968); Silver, A. et al., *Clin. Chem* 32: 1303–1306 (1986); Close, C. et al., *Diabet. Med.* 4:491–492 (1987); Harmoinen, A. et al., *Clin. Chim. Acta* 166:85–89 (1987); Marre, M. et al., *Clin. Chem.* 33:209–213 (1987); McCormik, C. P. et al., *Ann. Clin. Lab Sci.* 19:944–951 (1989); Cambiaso, C. L. et al., *Clin. Chem.* 34:416–418 (1988); Niwa, T. et al., *Clin. Chim. Acta* 186:391–396 (1990), the teachings of all of which are incorporated herein in their entirety). The levels of albumin or total protein in urine before and after treatment with the iron chelator can be determined and the frequency or amount of doses required to alleviate microalbuminuria can be adjusted as needed for each individual undergoing treatment. Since microalbuminuria is associated with diabetic nephropathy in diabetic individuals (Mattock, M. B., et al., *Diabetes* 41:736–741 (1992); Neil, A., et al., *Diabetes Care* 16:996–1003 (1993); Abbott, K. C., et al., *Arch. Intern. Med.* 154:146–153 (1994), the teachings of all of which are incorporated herein in their entirety) it is expected that the methods of the invention can be employed to halt the progression of microalbuminuria and, thus, prevent development of diabetic nephropathy.

The amount effective to alleviate microalbuminuria can be an amount of the iron chelator that restores the levels of albumin in urine or prevents a further increase in albumin levels in the urine. In a preferred embodiment, the levels of albumin in urine are restored to levels of about that in a control individual. The term "restore" refers to returning the albumin levels in urine to the levels observed before the individual developed microalbuminuria or to levels of about that observed in a control individual. The administration of iron chelators to humans afflicted with microalbuminuria can be used to halt the progression of the microalbuminuria. In one embodiment, progression of micoralbuminuria is halted by administering to the human an iron chelator (e.g., about 20 mg/kg body weight to about 150 mg/kg body weight).

In another embodiment, the invention relates to a method of halting the progression of microalbuminuria in a human, comprising measuring catalytic iron content in a pretreatment urine sample obtained from the human and administering a dose of an iron chelator to a human having a catalytic iron content in the pretreatment urine sample above a catalytic iron content in a control sample. The catalytic iron content in at least one subsequent urine sample obtained from the human is measured during or after the administration of the iron chelator and compared with the catalytic iron content in the pretreatment urine sample, the control sample, or both. The dose of the iron chelator administered to the human is adjusted until the catalytic iron content in the urine of the human is about that of the control sample.

A "control" level, when referring to the treatment of humans exhibiting microalbuminuria, is defined as described above for humans afflicted with kidney diseases except the control level refers to a level of urinary albumin, rather than a level of total protein as described in humans afflicted with kidney disease.

Microalbuminuria can progress and ultimately lead to diabetic nephropathy, a progressive kidney disease (Mattock, M. B., et al., *Diabetes* 41:736–741 (1992); Neil, A., et al., *Diabetes Care* 16:996–1003 (1993); Abbott, K. C., et al., *Arch. Intern. Med.* 154:146–153 (1994), the teachings of all of which are incorporated herein in their entirety). Thus, another aspect of the invention relates to a method of halting the progression of microalbuminuria in a human comprising measuring catalytic iron content in a pretreatment urine sample obtained from the human and administering a dose of deferiprone to a human having a catalytic iron content in the pretreatment urine sample in an amount greater than about 15 nmol/mg of a reference protein in a dose of about 20 mg/kg body weight to about 150 mg/kg body weight of the human. The catalytic iron content is measured in at least one subsequent urine sample obtained from the human during or after the administration of deferiprone. The catalytic iron content in the subsequent urine sample of the human is compared with the catalytic iron content in the pretreatment urine sample and the dose of deferiprone administered to the human adjusted until the catalytic iron content in a subsequent urine sample of the human is below about 15 nmol/mg of a reference protein.

The methods of the present invention can be accomplished by the administration of the iron chelator iron by enteral or parenteral means. Specifically, the route of administration is by oral ingestion (e.g., tablet, capsule form). Other routes of administration as also encompassed by the present invention including intramuscular, intravenous, intraarterial, intraperitoneal, or subcutaneous routes, and nasal administration. Suppositories or transdermal patches can also be employed.

The iron chelators can be used alone or in any combination when administered to the humans. For example, deferiprone can be coadministered with another iron chelator such as deferoxiamine to treat a kidney disease (e.g., diabetic nephropathy, primary glomerulonephritis, secondary glomerulonephritis, microalbuminuria). It is also envisioned that one or more iron chelators can be coadministered with other therapeutics (e.g., steroids) to, for example, treat kidney diseases, halt the progression of a kidney disease, reduce the severity of a kidney disease Coadministration is meant to include simultaneous or sequential administration of two or more iron chelators. It is also envisioned that multiple routes of administration (e.g., intramuscular, oral, transdermal) can be used to administer one or more iron chelators.

The iron chelators can be administered alone or as admixtures with conventional excipients, for example, pharmaceutically, or physiologically, acceptable organic, or inorganic carrier substances suitable for enteral or parenteral application which do not deleteriously react with the iron chelator. Suitable pharmaceutically acceptable carriers include water, salt solutions (such as Ringer's solution), alcohols, oils, gelatins and carbohydrates such as lactose, amylose or starch, fatty acid esters, hydroxymethycellulose, and polyvinyl pyrolidine. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like which do not deleteriously react with the iron chelator.

When parenteral application is needed or desired, particularly suitable admixtures for the iron chelator are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampules are convenient unit dosages. The iron chelators can also be administered via transdermal pumps or patches. Pharmaceutical admixtures suitable for use in the present invention are well-known to those of skill in the art and are described, for example, in Pharmaceutical Sciences (17th Ed., Mack Pub. Co., Easton, Pa.) and WO 96/05309 the teachings of both of which are hereby incorporated by reference.

The dosage and frequency (single or multiple doses) of iron chelators administered to a human can vary depending upon a variety of factors, including the size, age, sex, health, body weight, body mass index, and diet of the human; nature and extent of symptoms of the kidney disease being treated (e.g., diabetic nephropathy, microalbuminuria), kind of concurrent treatment (e.g., steroids), complications from the kidney disease, microalbuminuria, or other health-related problems. In a preferred embodiment, humans with a kidney disease are treated three times a day with a dose of iron chelator (e.g., deferiprone in 500 mg capsules) at about 30 mg/kg to about 75 mg/kg body weight per day for about 2–6 months. Other therapeutic regimens or agents can be used in conjunction with the iron chelator treatment methods of the present invention. For example, the administration of the iron chelator can be accompanied by steroid administration. Adjustment and manipulation of established dosages (e.g., frequency and duration) are well within the ability of those skilled in the art.

The present invention is further illustrated by the following examples, which are not intended to be limiting in any way.

EXEMPLIFICATION

Example 1

Urinary Catalytic Iron in Patients with Kidney Disease

Selection of Patients with Kidney Disease

Human patients (n=70) were used in these studies. Controls were healthy human patients with no history of kidney disease, hypertension, diabetes or other diseases that affect the kidney. Males and females were used in the studies. Ages of the human patients ranged from 4 years of age to 70 years of age. Ethnicity of the patients included Caucasians, African-American and Hispanics.

Kidney disease was detected in patients by the presence of an abnormal amount of protein in the urine and/or an abnormal renal function. An abnormal amount of protein in urine is an amount of total protein greater than about 0.15 g/24 h measured by an adaptation of pyrogallol redmolydate method described by Fujita, Y., et al., *Bunseki Kgaku* 32:379–386 (1983), the teachings of which are hereby incorporated by reference in their entirety. Many patients, as part of their routine work up, had received kidney biopsies providing diagnosis of the nature of the kidney disease.

Glomerular filtration rate was assessed in humans by measuring serum creatinine (normal values 0.96 mg/dl for women, and 1.16 mg/dl for men—values above 1.4 mg/dl considered abnormal), creatinine clearance or both. Creatinine clearance was calculated by the standard formula Cr=Ucr V/PCr where Cr=clearance of creatinine (ml/min); Ucr=urine creatinine (mg/dl), V=volume of urine, and PCr=plasma creatinine (mg/dl).

Patients with kidney disease included the following groups of patients:

Glomerulonephritis. This diagnosis was based on patients with abnormally high amount of urinary protein (greater than about 150 mg/24 hours) including patients with nephrotic syndrome (greater than about 3.5 gm protein). The diagnosis of glomerulonephritis was made on histological examination of the kidney, which included light microscopy, immunofluorescence, and electron microscopy using routine methods. Diagnoses included both primary causes such as membranous nephropathy, focal segmental sclerosis, IgA nephropathy, membranoproliferative glomerulonephritis, and crescentic glomerulonephritis as well as secondary causes such as, systemic lupus erythematosis, hemolytic uremic syndrome or Henoch-Schonlein purpura.

Microalbuminuria Patients with diabetes who had microalbuminuria had urinary albumin in a range between about 30 mg to about 300 mg for 24 hours as measured by a method which uses the rate of increase in light scattered from particles suspended in solution as a result of complexes formed during an antigen-antibody reaction or by the dipstick method.

Diabetic Nephropathy. Patients with diabetes who had diabetic nephropathy with overt proteinuria (greater than about 150 mg/24 hours) in 24-hour sample. The diagnosis of diabetic nephropathy was based on presence of overt proteinuria, history of diabetes, and presence of retinopathy on clinical examination.

Ischemic nephropathy was based on clinical and radiological findings.

A urine sample was obtained from humans with and without (control) kidney disease and assessed for catalytic iron content and creatinine content using established methods as described below.

Urinary Catalytic Iron and Creatinine in Humans with and without Kidney Disease

Catalytic iron content was measured in urine using a well established bleomycin assay (Gutteridge J. M. C., et al., *Biochem J* 199:263–265 (1981), the teachings of which are incorporated herein in their entirety).

In vivo iron is primarily bound to heme or non-heme proteins and does not directly catalyze the generation of hydroxyl radicals or a similar oxidant (Gutteridge J. M. C., et al., *Biochem J* 199:263–265 (1981), the teachings of which are incorporated herein in their entirety). In the catalytic iron assay used in these studies, the antibiotic bleomycin detects iron complexes capable of catalyzing free radical reactions. Bleomycin, in the presence of an iron salt and a suitable reducing agent, binds to and degrades DNA with the formation of a product that reacts with thiobarbituric acid to form a chromogen. The binding of the bleomycin-iron complex to the DNA makes the reaction site specific and antioxidants rarely interfere. Thus, the iron detected by this method was a measure of iron available from the sample to bleomycin. The assay conditions prevent interference from iron containing proteins. Iron bound to transferrin, lactoferrin, ferritin or iron containing enzymes is not detected in the bleomycin assay (Gutteridge J. M. C., et al., *Biochem J* 199:263–265 (1981), the teachings of which are incorporated herein in their entirety).

Specifically, the assay was performed as follows:

Reagent Preparation

1. Chelex-treated pyrogen free $H_2O$ (Chelex $H_2O$)
   Add 5 g chelex 100 resin (Bio-Rad, Cat#: 142-2842: 200–400 mesh, sodium form) to 100 ml pyrogen free water (Baxter) and shake well. Stand overnight at 4° C. and filter off the Chelex with bottle filter system (0.22 μm filter). After Chelex treatment of all solutions used in the assay, the Chelex must be carefully removed to avoid contamination by resin.

2. DNA (1 mg/ml)
   Add 50 mg DNA (Type I: calf thymus, Sigma D-1501) to 50 ml Chelex $H_2O$ and allow to stand at 4° C. overnight to effect solution. Treat this solution with 15 mg Chelex 100 resin overnight at 4° C. and centrifuge at 3000 rpm for 30 min to remove Chelex. If there are still some Chelex particles in the solution, centrifuge it again at 3000 rpm about 15 min. The reconstituted DNA is suitable for use in the assay for about 7 days after mixing when stored at 4° C.

3. Bleomycin sulfate (1 U/ml)
   15 U bleomycin sulfate (Bleoxane, Nippon Kayaku Co. Ltd, Tokyo, Japan) in 15 ml Chelex $H_2O$. The reconstituted bleomycin is suitable for use in the assay for about 1 month after preparation.

4. Magnesium chloride (50 mM)
   Add 0.1 g $MgCl_2.6H_2O$ (FW. 203.3) in 10 ml Chelex $H_2O$. Treat the solution with 3 g Chelex 100 resin and centrifuge at 3000 rpm for 10 min to remove Chelex.

5. Hydrochloric acid (40 mM)
   33.2 μl HCl (Ultrapure, Baker 6900-05) in 10 ml Chelex $H_2O$.

6. NaOH (40 mM)
   16 mg NaOH in 10 ml Chelex $H_2O$.

7. Ascorbic acid (8 mM)
   70 mg ascorbic acid (FW. 176.1) in 1 ml Chelex $H_2O$. Treat the solution with 50 mg Chelex 100 resin and centrifuge at 3000 rpm for 30 min to remove Chelex. Dilute 1:50 with Chelex $H_2O$ before use. Prepare immediately prior to use in the assay.

8. EDTA (0.1 M)
   0.37 g EDTA in 10 ml Chelex $H_2O$.

9. Thiobarbituric acid (TBA) (1% w/v in 50 mM NaOH)
   1 g TBA in 100 ml of 50 mM NaOH (NaOH prepared in Chelex $H_2O$).

10. HCl (25% v/v)
    25 ml HCl (Ultrapure, Baker Catalog #6900-05) in 100 ml Chelex $H_2O$.

11. Standard Iron
    16 mg $FeCl_3$ (FW. 162.2) in 10 ml Chelex $H_2O$. Dilute 1:100 for stock solution (100 nmol/ml), then dilute 1:1 to make the standard concentrations as 50.25, 12.5, 6.25, and 3.125 nmol/ml and Chelex $H_2O$. Prepare standards immediately prior to use in the assay.

Procedure

1. To remove particulates, urine samples were centrifuged at about 3000 rpm for about 10 min and the resulting supernatant used in the bleomycin assay.

2. Place the following in a plastic tube in the following order:
   0.5 ml DNA
   0.05 ml bleomycin sulfate (for blanks add Chelex $H_2O$)
   0.1 ml $MgCl_2$
   0.1 ml standard Fe solution or urine samples
   0.1 ml ascorbic acid 3. Mix well before and after the addition of ascorbic acid. For each sample or standard prepare a parallel blank. The sample and standard blanks are identical to their test reaction mixtures except that bleomycin is omitted 4. Adjust pH of all standards, samples and their blanks to about pH 7.2–7.8 using 40 mM HCl or 40 mM NaOH.

5. Incubate all tubes in temperature controlled shaker at 100 rpm, about 37° C. for about 2 h.

6. Stop the reaction by addition of 0.1 ml EDTA.

7. Add 1 ml TBA and 1 ml 25% HCl and mix well.

8. Transfer the mixture into new or acid-washed glass tube and heat at about 100° C. for about 15 min.

9. Transfer the solution in to 4.5 ml cuvette after cooling and read absorbency at 532 nm against the corresponding blank (without bleomycin).

10. Calculate the amounts of bleomycin-detectable iron content in test samples from the standard curve obtained in each experiment. The absorbency of the zero standard (contains only Chelex $H_2O$) reflecting iron contamination in the reagents is subtracted from all test samples.

11. Urine bleomycin-detectable iron is expressed as nmol/mg creatinine. Creatinine in the urine sample is measured using a creatinine assay kit (Sigma Chemical Co., St. Louis, Mo. 555-A).

Statistical Analysis

Data were expressed as the mean±SEM of moles catalytic iron/mg creatinine. Significant differences between group means was determined using an unpaired t-test. The patient data was compared to controls using a paired t-test and p-value of <0.05 was considered significant.

Results and Conclusions

As shown in FIG. 1, Table 1 and Table 2, urinary catalytic iron was elevated in patients with a wide variety of kidney diseases compared to patients without kidney disease. Thus, urinary catalytic iron plays a role in kidney disease and is indicative of a kidney disease in a human.

Example 2

Treatment of Patients with Kidney Disease with an Iron Chelator

Selection of Patients with Kidney Disease

The diagnosis of the kidney disease was made by performing a kidney biopsy and included patients with membranoproliferative glomerulonephritis, membranous nephropathy, focal segmental sclerosis, IgA nephropathy, and diabetes as described above.

Iron Chelator Treatment of Patients with Kidney Disease

Patients with kidney disease who had abnormally high urinary protein were treated with the iron chelator deferiprone (1,2-dimethyl-3-hydroxypyrid-4-one) (L1). Deferiprone was synthesized as previously described capsule (Kontoghiorghes A. J., et al., *Inorganica Chimica Acta* 136:L11–L12 (1987), the teachings of which are hereby incorporated by reference in it entirety) and formulated into capsules containing 500 mg of deferiprone per capsule.

Urinary protein and serum creatinine was measured as described above before the administration of deferiprone. Patients were treated by oral ingestion of deferiprone in a range between about 30 mg and about 75 mg deferiprone per kilogram body weight per day 3 times a day. Urinary protein and serum creatinine was obtained 2–6 months after the administration of the iron chelator. As shown in Table 3, treatment with the iron chelator significantly decreased the amount of total urinary protein and serum creatinine in patients with kidney disease. Total urinary protein and serum creatinine measured before (e.g., pretreatment) and after the administration of deferiprone were compared using a paired t-test and p-value of <0.05 was considered significant.

These data show that the iron chelator treated the kidney diseases. Therefore, it is believed that the effect of catalytic iron can be significantly reduced or prevented from acting directly or indirectly on the kidney to injure the kidney, thereby causing kidney disease, which if left untreated (no iron chelator) would result in an increase in total urinary protein content and serum creatinine.

TABLE 1

Urinary Catalytic Iron In Patients with Progressive Kidney Disease

| Age/Sex/Race | | | Diagnosis | 24 hr prot (mg/24 hrs) | Serum Cr (mg/dl) | CrCl (ml/min) | Catalytic Iron (Nmol/mg creatinine) |
|---|---|---|---|---|---|---|---|
| 20 | F | W | Membranous | 8900 | 1.1 | 120.0 | 33.4 |
| 23 | M | W | Membranous | 4200 | 2.3 | | 22.3 |
| 50 | F | B | SLE | 5000 | 1.9 | 57.0 | 90.7 |
| 51 | F | B | SLE | 5000 | 1.4 | | 9.1 |
| 64 | M | W | SLE | 3700 | 0.9 | | 11.0 |
| 45 | F | W | SLE | 3700 | 0.6 | | 69.0 |
| 38 | F | B | SLE | 6843 | 4.4 | | 70.0 |
| 38 | F | B | FSGS | 5000 | 2.6 | | 52.7 |
| 7 | M | W | FSGS | 20790 | 2.1 | 30.6 | 48.6 |
| 15 | F | B | FSGS | 2360 | 0.8 | 110.2 | 43.7 |
| 14 | F | B | FSGS | 16350 | 2.3 | 38.6 | 17.3 |
| 32 | M | B | FSGS | 300 | 2.2 | | 20.1 |
| 40 | F | B | FSGS | 5200 | 1.7 | | 61.6 |
| 40 | M | W | FSGS | | 2.1 | | 28.0 |
| 40 | M | B | FSGS | 15730 | 3.3 | 20.0 | 118.0 |
| 11 | F | W | HSP | 11120 | 0.6 | 139.3 | 26.1 |
| <1 | M | W | HUS | | 0.7 | | 84.2 |
| 16 | M | B | IgA | 830 | 1.6 | 58.4 | 19.1 |
| <1 | M | B | MPGN | 2104 | 0.5 | 75.0 | 66.8 |
| 54 | M | | MPGN | | 3.8 | | 43.0 |
| 40 | M | W | MPGN | 16260 | | | 106.0 |
| 65 | F | W | Creacentic | | 5.9 | | 5.4 |
| Mean | | | | | | | 48 |
| SEM | | | | | | | 7 |
| Number | | | | | | | 22 |
| P | | | | | | | <0.0001 |
| Ischemic Nephropathy | | | | | | | |
| 45 | F | W | Isch Neph | | 1.8 | | 92.0 |
| 80 | F | W | Isch Neph | | 2.0 | | 96.0 |
| Mean | | | | | | | 94.0 |
| SEM | | | | | | | 2.0 |
| Number | | | | | | | 2 |
| P | | | | | | | <0.01 |

SLE: Systemic Lupus Erythematosus;
FSGS = Focal Segmental Glomerulosclerosis;
HSP = Henoch-Schonlein Purpura;
HUS = Hemolytic Uremic Syndrome;
MPGN = Membranoproliferative Glomerulonephritis;
Isch Neph = Ischemic Nephropathy
SLE, HSP, HUS and Ischemic Nephropathy are secondary causes of renal disease.
P compared to control value of 8.1 ± 1.4, n = 23, using unpaired t test
Isch Neph = Ischemic Nephropathy
prot = protein
Cr = creatinine
CrCl = creatinine Clearance

TABLE 2

Urinary Catalytic Iron In Patients with Diabetic Nephropathy Microalbuminuria

| Age/Sex/Race | | | 24 hr prot (mg/24 hrs) | Serum Cr (mg/dl) | CrCl (ml/min) | Catalytic Iron (nmol/mg creatinine) |
|---|---|---|---|---|---|---|
| 69 | F | W | | 0.8 | | 59.3 |
| 77 | M | W | | 1.4 | | 84.1 |
| 56 | F | W | | 0.7 | | 75.9 |
| 39 | F | B | | 0.6 | | 10.2 |
| 47 | F | W | | 1.0 | | 46.3 |
| 50 | M | B | | 1.3 | 103.0 | 23.0 |
| 56 | M | W | | 2.4 | 46.0 | 21.0 |
| 61 | M | W | | 1.2 | 90.0 | 36.0 |
| 69 | M | W | | 1.1 | 77.0 | 25.0 |
| 73 | M | B | | 1.4 | 54.0 | 58.0 |
| 78 | M | W | | 1.1 | 71.0 | 82.0 |
| 59 | F | B | | 1.2 | 116.7 | 44.0 |
| 30 | M | B | | 1.4 | 68.0 | 86.0 |
| Mean | | | | | | 50.0 |
| SEM | | | | | | 7.0 |
| Number | | | | | | 13 |
| P | | | | | | <0.0001 |

TABLE 2-continued

Urinary Catalytic Iron In Patients with Diabetic Nephropathy Microalbuminuria

| Age/Sex/Race | | | 24 hr prot (mg/24 hrs) | Serum Cr (mg/dl) | CrCl (ml/min) | Catalytic Iron (nmol/mg creatinine) |
|---|---|---|---|---|---|---|
| Diabetic Patients with Overt Proteinerria | | | | | | |
| 61 | M | B | 4800.0 | 5.3 | | 56.2 |
| 56 | M | B | 8000.0 | 3.0 | | 20.0 |
| 67 | F | B | 3816.0 | 3.1 | 25.0 | 42.0 |
| 42 | F | W | 8300.0 | 7.2 | 10.0 | 32.6 |
| 51 | F | B | 11200.0 | 2.8 | 31.0 | 53.8 |
| 32 | M | W | 6899.0 | 6.8 | | 44.5 |
| 61 | M | B | 11363.0 | 5.4 | | 30.2 |
| 73 | M | W | 1064.0 | 3.0 | | 27.3 |
| 71 | F | B | 3200.0 | 1.6 | | 49.0 |
| 79 | F | W | 1350.0 | 3.0 | | 25.0 |
| Mean | | | | | | 38.0 |
| SEM | | | | | | 4.0 |
| Number | | | | | | 10 |
| P | | | | | | <0.0001 |

P compared to control value of 8.1 ± 1.4, n = 23, using unpaired t test
Microalbuminuria is defined as urinary albumin between 30 to 300 mg/24 hrs as measured quantitavely in a 24 hour sample or by a dipstick in a spot urine.
prot = protein
Cr = creatinine
CrCl = creatinine Clearance

TABLE 3

Urinary protein and creatinine levels in patients with kidney disease before and after treatment with an iron chelator

| Pt. # | Sex | Age | Wt (kg) | Diagnosis* | 24-Hr Urinary Protein grams/24 hrs | | | | Reduction Creatinine mg/dl | |
|---|---|---|---|---|---|---|---|---|---|---|
| | | | | | Before | After | Grams | % | Before | After |
| 1 | F | 52 | 60 | MPGN | 2.6 | 1.2 | 1.4 | 54 | 1.3 | 0.8 |
| 2 | F | 40 | 73 | Membranous | 2.8 | 0.6 | 2.2 | 78 | 1.4 | 0.9 |
| 3 | F | 29 | 42 | Chronic GN | 3.4 | 1.5 | 1.9 | 49 | 1.0 | 0.9 |
| 4 | M | 33 | 74 | Membranous | 1.2 | 0.2 | 1 | 83 | 1.4 | 1.3 |
| 5 | F | 40 | 66 | Membranous | 6.5 | 4 | 2.5 | 38 | 0.8 | 0.9 |
| 6 | M | 28 | | FSGS | 2.8 | 1.6 | 0.7 | 25 | | |
| 7 | F | 18 | 36 | FSGS | 4.2 | 1.6 | 2.6 | 62 | 0.7 | 0.6 |
| 8 | M | 14 | 37 | Mesangial proliferation/IgA | 6 | 0.05 | 5.95 | 99 | 0.6 | 0.5 |
| 9 | M | 3 | 14 | DPGN | 5.8 | 2.8 | 2 | 34 | | |
| 10 | F | 12 | | MPGN | 4.6 | 2.5 | 2.1 | 44 | 0.4 | 0.5 |
| 11 | M | 32 | 77 | Diabetes | 0.538 | 0.1 | 0.43 | 80 | 1.6 | 1.4 |
| 12 | M | 45 | | Mesangial proliferation/IgA | 4.5 | 3.8 | 0.7 | 15 | | |
| 13 | M | 35 | 50 | Membrane | 5.3 | 4.8 | 0.5 | 9 | 0.8 | 0.7 |
| 14 | M | 32 | 62 | Membranous FSGS | 4.5 | 4.6 | 0.1 | 2 | 2.1 | 1.5 |
| | | | | Mean | 3.91 | 2.13 | 1.70 | 48 | 1.10 | 0.90 |
| | | | | SD | 1.78 | 1.67 | 1.49 | 30 | 0.50 | 0.35 |
| | | | | SEM | 0.47 | 0.45 | 0.39 | 8 | 0.15 | 0.10 |
| | | | | N | 14 | 14 | 14 | 14 | 11 | 11 |
| | | | | | p < 0.001 | p < 0.001 | p < 0.001 | | | |

TABLE 3-continued

Urinary protein and creatinine levels in patients with kidney disease before and after treatment with an iron chelator

| | | | | 24-Hr Urinary Protein grams/24 hrs | | Reduction Creatinine mg/dl | | | |
|---|---|---|---|---|---|---|---|---|---|
| Pt. # | Sex | Age | Wt (kg) | Diagnosis* | Before | After | Grams | % | Before | After |

DPGN: Diffuse proliferative glomerulonephritis;
MPGN: Membranoproliferative glomerulonephritis;
FSGS: Focal segmental glomerulosclerosis Equivalents While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method for diagnosing a kidney disease in a human comprising the step of measuring catalytic iron in a urine sample from the human.

2. The method of claim 1, wherein catalytic iron is measured in relation to a reference protein in the urine sample.

3. The method of claim 2, wherein the reference protein is urinary creatinine.

4. The method of claim 1, wherein the urine sample is obtained from a human having a kidney disease that is a progressive kidney disease of at least one member selected from the group consisting of primary glomerulonephritis and secondary glomerulonephritis.

5. The method of claim 4, wherein the primary glomerulonephritis is at least one member selected from the group consisting of membranous nephropathy, focal segmental sclerosis, IgA nephropathy, membranoproliferative glomerulonephritis and crescentic glomerulonephritis.

6. The method of claim 4, wherein the secondary glomerulonephritis is at least one member selected from the group consisting of diabetic nephropathy, systemic lupus erythematosis, hemolytic uremic syndrome and Henoch-Schonlein purpura.

7. The method of claim 1, wherein the urine sample is obtained from a human having ischemic nephropathy.

8. The method of claim 1, wherein the catalytic iron is measured prior to onset of clinical symptoms of the kidney disease in the human.

9. The method of claim 1, wherein the catalytic iron is measured after onset of clinical symptoms of the kidney disease in the human.

10. The method of claim 8, wherein the kidney disease is a progressive kidney disease.

11. The method of claim 10, wherein the progressive kidney disease is at least one member selected from primary glomerulonephritis and secondary glomerulonephritis.

12. The method of claim 11, wherein the primary glomerulonephritis is at least one member selected from the group consisting of membranous nephropathy, focal segmental glomerulosclerosis, IgA nephropathy, membranoproliferative glomerulonephritis and crescentic glomerulonephritis.

13. The method of claim 11, wherein the secondary glomerulonephritis is at least one member selected from the group consisting of systemic lupus erythematosus, henoch-schonlein purpura and hemolytic uremic syndrome.

14. The method of claim 8, wherein the kidney disease is ischemic nephropathy.

15. The method of claim 8, wherein the kidney disease is consequent to damage to an interstitium of a kidney.

16. The method of claim 1, wherein the urine sample is obtained from a human having a kidney disease consequent to damage to an interstitium of a kidney.

* * * * *